United States Patent
Boyd et al.

(10) Patent No.: US 9,260,362 B2
(45) Date of Patent: Feb. 16, 2016

(54) HYDROPHILIC ACTIVATED SORBENT EXTRACTION DISK

(71) Applicants: Joseph M. Boyd, Mount Pleasant, SC (US); Edward J. Kim, Riverdale, GA (US)

(72) Inventors: Joseph M. Boyd, Mount Pleasant, SC (US); Edward J. Kim, Riverdale, GA (US)

(73) Assignee: Environmental Express, Inc., Charleston, SC (US)

( * ) Notice: Subject to any disclaimer, the term of this patent is extended or adjusted under 35 U.S.C. 154(b) by 123 days.

(21) Appl. No.: 13/961,241

(22) Filed: Aug. 7, 2013

(65) Prior Publication Data
US 2014/0046112 A1 Feb. 13, 2014

Related U.S. Application Data (60) Provisional application No. 61/680,383, filed on Aug. 7, 2012.

(51) Int. Cl.
| | | |
|---|---|---|
| *C07C 7/12* | (2006.01) | |
| *B01D 15/00* | (2006.01) | |
| *B01D 15/08* | (2006.01) | |
| *B01J 20/28* | (2006.01) | |
| *B01J 20/26* | (2006.01) | |

(Continued)

(52) U.S. Cl.
CPC . *C07C 7/12* (2013.01); *B01D 15/00* (2013.01); *B01D 15/08* (2013.01); *B01J 20/261* (2013.01); *B01J 20/264* (2013.01); *B01J 20/2805* (2013.01); *B01J 20/28026* (2013.01); *B01J 20/28035* (2013.01); *B01J 20/28042* (2013.01); *B01J 20/28047* (2013.01); *B01J 20/28085* (2013.01); *B01D 15/322* (2013.01); *G01N 2030/528* (2013.01)

(58) Field of Classification Search
None
See application file for complete search history.

(56) References Cited

U.S. PATENT DOCUMENTS

| 4,810,381 A | 3/1989 | Hagen et al. |
| 4,842,739 A | 6/1989 | Tang |
| 5,391,298 A | 2/1995 | Pieper et al. |

(Continued)

FOREIGN PATENT DOCUMENTS

WO 9837949 A1 9/1998

OTHER PUBLICATIONS

Method 1664, Revision A: N-Hexane Extractable Material (HEM; Oil and Grease) and Silica Gel Treated N-Hexane Extractable Material (SGTHEM; Non-polar Material) by Extraction; and Gravimetry, United States Environmental Protection Agency, EPA-821-R-98-002, PB99-121949, Feb. 1999.

*Primary Examiner* — Tam M Nguyen
(74) *Attorney, Agent, or Firm* — Cohen & Grigsby, P.C.

(57) ABSTRACT

A one-piece solid phase extraction article to be used in solid phase extraction analysis, a filtration funnel comprising the one piece solid phase extraction article, and a method of use of the article. The article, device and method provide for improved analysis of hexane extractable material by eliminating the standard use of polar solvents to pre-condition the sorbent materials. The one-piece solid phase extraction article comprises water wettable monomeric phase type sorptive material embedded within a porous matrix. The water wettable monolithic polymeric sorptive material may be a hydrophilic polymeric gel, such as functionalized C-18 sorbent material, and the porous matrix may be fibrous matric, such as a glass fiber. The one-piece solid phase extraction article may further comprise one or more pre-filtration layers which do not contain the sorptive particles.

20 Claims, 6 Drawing Sheets

(51) Int. Cl.
*B01D 15/32* (2006.01)
*G01N 30/52* (2006.01)

(56) References Cited

U.S. PATENT DOCUMENTS

| | | | |
|---|---|---|---|
| 5,529,694 A | 6/1996 | Strickler | |
| 5,538,634 A | 7/1996 | Pfiffner et al. | |
| 5,616,407 A | 4/1997 | Fritz et al. | |
| 6,475,340 B1 | 11/2002 | Carlson et al. | |
| 2003/0120062 A1 | 6/2003 | Parthasarathy | |
| 2011/0117596 A1* | 5/2011 | Mattiasson | B01J 20/26 435/41 |
| 2014/0274659 A1* | 9/2014 | Romanos | B01J 20/3491 502/5 |

* cited by examiner

HYDROPHILIC ACTIVATED SORBENT EXTRACTION DISK

CROSS-REFERENCE TO RELATED APPLICATIONS

The present application claims the benefit under 35 USC 119(e) of prior U.S. Provisional Application 61/680,383 titled "Hydrophilic Activated Sorbent Extraction Disk" filed Aug. 7, 2012 by Joseph M. Boyd and Edward J. Kim, which is incorporated herein by reference in its entirety.

BACKGROUND OF THE INVENTION

1. Technical Field of the Invention

The invention pertains generally to sample testing products and techniques, and more specifically to an improved solid phase extraction filtration disk and a method for its use.

2. Description of the Related Art

Hexane Extractable Material (HEM) is a method-defined analyte based on the procedures set forth in Environmental Protection Agency ("EPA") Method 1664. This method is used in the EPA's survey and monitoring programs of surface and saline waters and industrial and domestic aqueous wastes under the Clean Water Act; the Resource Conservation and Recovery Act; the Comprehensive Environmental Response, Compensation, and Liability Act; and other EPA regulatory programs to determine the levels of n-hexane extractable material (oil and grease) and n-hexane extractable material that is not adsorbed by silica gel (non-polar material). Extractable materials include relatively non-volatile hydrocarbons, vegetable oils, animal fats, waxes, soaps, greases, and related materials.

EPA Method 1664 is based on liquid-liquid extraction. Simply, after extracting the oil and grease from the sampled water into a solvent, generally n-hexane, the n-hexane is evaporated and the total mass of material remaining is measured and reported as Hexane Extractable Material (HEM), or Silica Gel Treated Hexane Extractable Material (SGT-HEM). Differentiating HEM from SGT-HEM requires separate sample preparation by the technician. Further, the technician must ensure that there is no water present and all the n-hexane is evaporated, as the presence of either will result in over-reporting the HEM content of the sample. This means one measurement can take up to 48 hrs. Thus, EPA Method 1664 is both labor intensive and time consuming.

In general, modification of a method-defined analyte method is not allowed. EPA Method 1664, however, does list provisions allowing for some performance-based modifications, provided those changes do not degrade method performance or alter the chemistry of the method. In such a revision, the EPA allows solid phase extraction of the HEM from water using disks or cartridges, followed by the elution of the HEM from the disks or cartridges with n-hexane. The n-hexane is then evaporated from the sample and the remaining material is weighed to determine the HEM. SGT-HEM is determined by re-dissolving the HEM in n-hexane to perform the silica gel treatment. Thus, the revised EPA Method 1664 not only reduces the amount of solvent required, but also reduces the time required to perform the test.

Generally, the art of separation science, which involves extraction and chromatography, has two main objectives. One is high yield extraction and recovery of a targeted analyte and the other is a rapid rate of extraction and elution. A specific type of extraction used for separation is solid phase extraction, also known as SPE. SPE is a method of sample preparation that removes and concentrates an analyte from a liquid sample by absorption or adsorption onto a disposable solid phase medium. This is followed by elution of the analyte with a solvent appropriate for analysis.

SPE can be carried out using extraction disks which include particle loaded membranes of various diameters as the extraction medium. For example, one such disk comprises a membrane that includes sorbent particles (e.g., C-8 and C-18 bonded silica particles) immobilized in a web of poly (tetrafluoroethylene) (PTFE) microfibrils. Another exemplary disk includes a web of glass microfibers impregnated with chemically bonded silica sorbents such as C-18 aliphatics. For general use, these SPE disks can be supported on a glass or polymer frit in a standard filtration apparatus using vacuum to generate the desired flow of sample through the disk.

Currently, for SPE to work correctly in a method such as EPA Method 1664, the C-18 silica material in the extraction disk must go through a pre-conditioning process using a polar solvent such as methanol. Such disks are described in U.S. Pat. No. 5,391,298. The methods to fabricate existing extraction disks are also described in U.S. Pat. Nos. 5,538,634 and 6,475,340. However, the use of a polar solvent can lead to unacceptable modifications to EPA Method 1664. Thus, the technician must be extremely vigilant to remove all of the polar solvent from the extraction disk, yet keep the disk wetted, prior to performing the analytical method. That is, the disk must be pre-conditioned by solvent and remain wet before the addition of testing sample or the test may become out of compliance. While experienced technicians can master this technique and automated extraction systems provide more consistency and control, there is potential for error using such a pre-conditioning step.

To solve this problem, the Applicants have developed an SPE extraction disk, a testing system utilizing this extraction disk, and a method for testing under EPA Method 1664 that does not require pre-conditioning with a polar solvent. This eliminates any potential of a co-solvent coming into contact with the sample and non-compliance because of such.

SUMMARY

The presently disclosed invention overcomes many of the shortcomings of the prior art by providing an SPE disk which may be wetted by water or an aqueous solution. More specifically, embodiments of the presently disclosed invention provide a one piece solid phase extraction article wherein no polar solvent is required to wet the sorptive material prior to adsorption of an analyte.

An embodiment of the one piece solid phase extraction article of the present invention enables the use of any water wettable monomeric phase type sorptive material embedded within any porous matrix.

Alternate embodiments of the one piece solid phase extraction article of the present invention contemplate water wettable monolithic polymeric sorptive particles which may be a hydrophilic polymeric gel, such as cellulose fibers, polyacrylamides, activated carbon, functionalized C-8 sorbent material, functionalized C-18 sorbent material, or functionalized polystyrenedivinylbenzene.

Further embodiments of the one piece solid phase extraction article of the present invention contemplate water wettable monolithic polymeric sorptive particles which are either a copolymer of stearyl methacrylate (SMA), poly(ethylene glycol) methyl ether methacrylate (PEGMEMA) and ethylene dimethacrylate (EDMA); or a copolymer of stearyl methacrylate (SMA), poly(ethylene glycol) methyl ether methacrylate (PEGMEA) and 1-propanol/1,4-butanediol.

Embodiments of the one piece solid phase extraction article of the present invention contemplate a porous matrix which may be a plastic, a synthetic fiber, a paper media, a sintered metal, a glass fiber, a synthetic membrane filter, or a mixture thereof.

Embodiments of the one piece solid phase extraction article of the present invention contemplate different configurations and geometries of the article. The typical embodiment is circular but other shapes, such as any polygon, would achieve the same effectiveness in conjunction with the proper filtration support equipment, i.e. filter holders and housing.

Alternate embodiments of the one piece solid phase extraction article include sheets which may be pleated so as to allow for inclusion in a cartridge device. Further, the one piece solid phase extraction article may be supported within an enclosed cartridge which may have inlet and outlet ports that allow the filter to be placed in-line for vacuum filtration.

Further embodiments of the one piece solid phase extraction article of the present invention include different configurations of a pre-filtration layer. The sorbent layer containing the water wettable sorptive particles embedded in a porous matrix may be surrounded by or in contact with a pre-filtration layer that does not contain the sorptive particles. The addition of such a layer in contact with one side of the sorbent layer may provide support for the sorbent layer and may aid in pre-filtration of the aqueous sample to remove large particulates before reaching the sorbent layer. Further, in some embodiments, the sorbent layer may be disposed between and in contact with a first and second pre-filtration layer. This configuration may lead to bi-directional use of the solid phase extraction article. Additionally, the solid phase extraction article may contain only a sorbent layer and other means could be used to provide for pre-filtration of the sample.

The pre-filtration layer may be composed of the same material as the porous matrix of the sorbent layer or may be composed of a different material. Materials useable for the pre-filtration layer include at least plastic, a synthetic fiber, a paper media, a sintered metal, a glass fiber, a synthetic membrane filter, or a mixture thereof.

Embodiments of the one piece solid phase extraction article of the present invention allow for variation in the porosity of the porous matrix and/or the pre-filtration layer(s). Typically, filtration of a sample through a solid phase extraction article is assisted by a vacuum system providing intrusion or differential pressure to drive or pull the media through the article. By changing the porosity, the ability may exist to perform the filtration passively without the aid of mechanical pressure. A change in porosity within multiple layers may also allow different substances to be filtered within a particular region. Porosities in the range of 0.1 um to 200 um are preferred.

Alternate embodiments of the presently disclosed invention would also be achieved in the use of multiple sorbents within a multi-layer solid phase extraction article. Embodiments would provide a one piece solid phase extraction article having more than one sorbent layer, wherein each sorbent layer comprises a water wettable sorptive material embedded within a porous matrix. Such an article would allow for multiple substances to be adsorbed by a single one-piece solid phase extraction article and would be useful in a range of tests. Thus, it may serve as an all-purpose filter useful in multiple tests and not necessarily specific to a single method or analytical test.

The presently disclosed invention also provides for a one piece solid phase extraction article which is incorporated into a filtration funnel. The filtration funnel may be attached to a filtration system comprising a vacuum source capable of pulling sample fluids placed in the funnel through the one piece solid phase extraction article.

In a further embodiment, the filtration funnel with integral one piece solid phase extraction article may comprise a reservoir for holding unfiltered fluid therein and an outlet, wherein the one piece solid phase extraction article may be disposed between the reservoir and the outlet. The one piece solid phase extraction article may comprise at least one single sorbent layer as described above, and optionally may have one or more pre-filtration layers in contact with the top and/or bottom of the sorbent layer.

A further embodiment of the presently disclosed invention provides a method of concentrating by sorption at least one hexane extractable material from an organic fluid comprising: passing an organic fluid through a solid phase extraction article comprising at least one sorbent layer having water wettable monolithic polymeric sorptive particles embedded in a porous glass fiber matrix, wherein no pre-conditioning with a polar solvent is required prior to adsorption of an analyte by the sorptive particles. The method may further comprise eluting any adsorbed hexane extractable material by soaking the solid phase extraction article in n-hexane.

Embodiments of the presently disclosed invention will eliminate the need to pre-condition the SPE disk before use. They will ensure that the test results are in complete compliance with the analytical test methods. Currently, if an extraction disk becomes dry, it results in having to repeat the pre-conditioning process. The extraction article of the presently disclosed invention and the device utilizing the extraction article do not need to stay wet to be effective. As a result, the amount of time and labor associated with pre-conditioning of the extraction article is also eliminated, resulting in additional savings. Further, the use of solvents is no longer necessary for the pre-conditioning step, thus a reduction in solvent consumption will also result in additional savings. As a further advantage to the presently disclosed invention, elimination of the pre-conditioning step may also allow for field testing of such samples according to EPA Method 1664. Currently, such testing needs to be performed "off-site" in a laboratory environment such that solvents can be utilized and removed. With embodiments of the presently disclosed invention, it will no longer be necessary to transport hazardous solvents to the field to perform the pre-conditioning step.

Another advantage of certain embodiments of the presently disclosed invention is the utilization of a monomeric phase type of sorbent material. Currently, existing filters use a polymeric phase sorbent material. These are embodied in chromatography cartridges and are not typically used in SPE for environmental testing methods, such as EPA Method 1664. The monomeric phase type allows for more consistency from batch to batch testing because it results in one bonded phase and the same chemical entity. Polymeric phases can vary from batch to batch.

One of the large expenses to companies collecting samples in the field for Method 1664 is the shipping of large volumes of water to the laboratory. Method 1664 requires the collection of a 1-L sample and oftentimes, laboratories require the submittal of two or more samples per sampling point for quality control checks. Samples for Method 1664 are preserved to a pH of <2 with HCl or $H_2SO_4$ at the time of collection and may require special handling to meet DOT requirements. Filtration of samples for Method 1664 in the field was never a realistic option for samplers as the disk activation requirement made this a difficult process. Technicians have also been hesitant to take solvents such as methanol for disk activation into the field for safety reasons.

The presently disclosed invention makes the possibility of field filtration a reality. Field technicians can take a sample from a location, preserve it to the correct pH in the field, and then perform the filtration using a filter assembly installed with the presently disclosed invention. Once filtration is complete, the entire filtration assembly and the empty sample bottle can be sent to the laboratory for extraction. This will save companies a tremendous amount of money in shipping costs. An exemplary filtration system is sold under the trade name StepSaver™ (Environmental Express; Charleston, S.C.) and disclosed in U.S. Pat. No. 5,529,694, which is incorporated herein in its entirety by reference.

BRIEF DESCRIPTION OF THE DRAWINGS

Aspects, features, benefits and advantages of the embodiments herein will be apparent with regard to the following description, appended claims, and accompanying drawings. In the following figures, like numerals represent like features in the various views. It is to be noted that features and components in these drawings, illustrating the views of embodiments of the presently disclosed invention, unless stated to be otherwise, are not necessarily drawn to scale.

DETAILED DESCRIPTION

In the following description, the presently disclosed invention is set forth in the context of various alternative embodiments and implementations involving a one-piece solid phase extraction article to be used in SPE analysis, a filtration funnel comprising a one piece solid phase extraction article, and a method of use of said article and funnel comprising said article.

Various aspects of the one-piece solid phase extraction article and filtration funnel comprising a one piece solid phase extraction article may be illustrated by describing components that are coupled, attached, and/or joined together. As used herein, the terms "coupled", "attached", and/or "joined" are interchangeably used to indicate either a direct connection between two components or, where appropriate, an indirect connection to one another through intervening or intermediate components. In contrast, when a component is referred to as being "in contact with", "directly attached to", and/or "directly joined with" another component, there are no intervening elements shown in said examples.

Relative terms such as "lower" or "bottom" and "upper" or "top" may be used herein to describe one element's relationship to another element illustrated in the drawings. It will be understood that relative terms are intended to encompass different orientations of aspects of the one-piece solid phase extraction article and filtration funnel comprising a one-piece solid phase extraction article in addition to the orientation depicted in the drawings. By way of example, if aspects of the one-piece solid phase extraction article shown in the drawings are turned over, elements described as being on the "bottom" side of the other elements would then be oriented on the "top" side of the other elements as shown in the relevant drawing. The term "bottom" can therefore encompass both an orientation of "bottom" and "top" depending on the particular orientation of the drawing.

Figure 1:
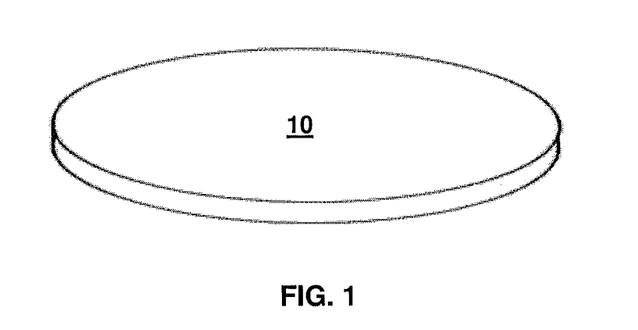
FIG. 1 illustrates a top perspective view of the solid phase extraction article in accordance with certain aspects of the presently disclosed invention.

Referring now to the drawings, embodiments of the one-piece solid phase extraction article of the presently disclosed invention are shown in FIGS. 1-5 generally designated by the reference numeral 10. FIG. 1 illustrates a top perspective view of an embodiment of the one-piece solid phase extraction article 10. As shown, the article 10 may be in the form of a circular disk or sorbent layer which comprises a water wettable sorptive material embedded within a porous matrix.

In embodiments of the one-piece solid phase extraction article, any water wettable sorbent material may be embedded within any porous matrix; e.g., any sorbent material which may become activated or wet by water and does not require pre-conditioning with a polar solvent such as methanol. The sorbent may be any derivative of a monomeric phase type sorbent or a polymeric type sorbent material that is water wettable.

The porous matrix may be plastic, synthetic fiber, paper media, sintered metal, glass fibers, or a synthetic membrane filter.

The water wettable sorbent material may be monolithic polymeric sorptive particles which are hydrophilic. For example, the sorptive particles may be a hydrophilic polymeric gel. Further non-limiting examples of hydrophilic sorptive particles include cellulose fibers, polyacrylamides, activated carbon, functionalized C-8 sorbent material, functionalized C-18 sorbent material, and functionalized polystyrenedivinylbenzene.

The C-18 material found in presently available SPE disks and cartridges for Method 1664 is generally a hydrophobic material. As discussed above, this material requires activation or wetting with a polar solvent such as methanol and cannot then be allowed to go dry. This wetting is necessary because the low surface energy of the hydrophobic particles or composite does not allow high surface tension aqueous solutions efficient access to the high surface area of the sorptive particles' internal pores. Wetting with a solvent such as methanol requires the technician to replace the methanol with deionized water before the introduction of the sample as Method 1664 does not allow the use of co-solvents which lead to alteration of the chemistry of the method. Further, prior art C-18 materials lose sorptive capacity upon exposure to aqueous solutions, and thus are less efficient in adsorption capacity when used in SPE analysis of aqueous samples.

A number of approaches have been evaluated to increase the wettability or hydrophilicity of these particles and composites. One approach to eliminating or minimizing the wetting problem can be the addition of hydrophilic adjuvants such as micro-crystalline cellulose fibers to composite sheet articles comprising polytetrafluoroethylene polymer (PTFE) or other hydrophobic fibrils and various sorptive particulate, as described in U.S. Pat. No. 4,810,381. While this approach increases the overall hydrophilic character of the composite, it does not address wetting of the internal pores of entrapped sorptive particulate.

The Applicants have solved this problem through the use of water wettable sorptive materials such as hydrophilic C-18. Thus, embodiments of the presently disclosed invention contain a C-18 material which is hydrophilic, and therefore, does not require any activation with a polar solvent. This eliminates the chance of introducing co-solvents into the method procedure and gives the laboratory confidence that their analytical results meet all method requirements. An example of a hydrophilic material used as the sorptive particles in the one piece solid phase extraction articles of the present invention is a Prevail™ material (W.R. Grace & Co.-Conn; Columbia, Md.). Prevail™ material has been commercially available in Prevail™ Carbohydrate ES Columns, which are columns packed with the rugged, hydrophilic polymeric gel. The columns are versatile, but are predominantly used to analyze mono- and oligosaccharides by normal-phase liquid chromatography, or negatively charged compounds by ion-exchange chromatography.

Hydrophilic C-18 monolithic polymer sorbents can be synthesized by incorporating both hydrophobic and hydrophilic monomers into a monolithic material, by copolymerization of stearyl methacrylate (SMA), poly(ethylene glycol) methyl ether methacrylate (PEGMEMA) and ethylene dimethacrylate (EDMA) in the presence of selected porogens. Alternatively, a C-18 monolithic material with a hydrophilic character may be obtained by copolymerizing stearyl methacrylate (SMA) and a hydrophilic monomer poly(ethylene glycol) methyl ether methacrylate (PEGMEA) with porogen of 1-propanol/1,4-butanediol. While the Applicants have listed specific examples of hydrophilic C-18 materials, this is not meant to limit embodiments of the presently disclosed invention. Other methods and materials used to produce water wettable C-18 materials are within the scope of the present invention.

Embodiments of the presently disclosed invention may comprise polymeric phase sorptive materials. An example of a polymeric phase sorbent useful as the sorptive particles in articles of the present invention includes the Oasis® sorbents (Waters Corporation; Milford, Mass.).

As shown in FIG. 1, an embodiment of the presently disclosed invention is a one-part solid phase extraction article 10 having one sorbent layer which comprises a water wettable sorbent material with a monomeric phase type embedded within a porous matrix.

Figure 2:
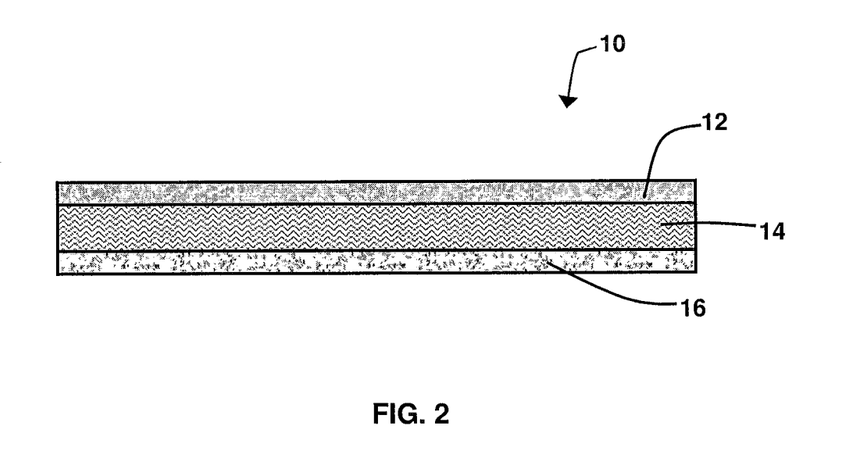
FIG. 2 illustrates a side view of the filter as shown in FIG. 1.

The solid phase extraction article 10 may comprise additional layers, as shown in FIG. 2. The sorbent layer 14 may be disposed between additional pre-filtration layers (12, 16) which do not contain sorptive materials. The pre-filtration layers (12, 16) may act as a pre-filter that removes particulate material, such as suspended solids from a sample of interest. The pre-filtration layers (12, 16) preferably reduce clogging of the sorbent layer 14, which would otherwise increase extraction times. In certain embodiments, the pre-filtration layers (12, 16) may also aid in capturing the analyte of interest, thus enhancing the sorption capacity of the one-piece solid phase extraction article 10.

The pre-filtration layers (12, 16) may be plastic, synthetic fiber, paper media, sintered metal, glass fibers, or a synthetic membrane filter.

In certain arrangements, the pre-filtration layer (12, 16) and the porous matrix of the sorbent layer 14 may be composed of the sample material. Alternatively, the pre-filtration layer (12, 16) may be composed of a different porous matrix material than the sorbent layer 14. Such an arrangement may aid in the capture of contaminants on the pre-filtration layer (12, 16) which could interfere with the analysis of the desired analyte, which is collected by the sorbent layer 14. In this arrangement, the pre-filtration layer (12, 16) and the sorbent layer 14 may be made of materials that have differing sorption characteristics for the analyte of interest.

Inclusion of a pre-filtration layer on the top 12 and bottom 16 of the sorbent layer 14 allows for bi-directional use of the solid phase extraction article 10 in a filtration apparatus. Alternatively, in certain embodiments, only a single pre-filtration layer (12 or 16) may be included. As such, the user would place the solid phase extraction article 10 with the sorbent layer 14 facing downward and the pre-filtration layer (12 or 16) facing upward so that the aqueous sample contacts the pre-filtration layer (12 or 16) first.

Alternatively, the solid phase extraction article 10 may contain only a sorbent layer as is shown in FIG. 1 and other means could provide a pre-filtration, such as using a Filter Aid powder.

Figure 3A:
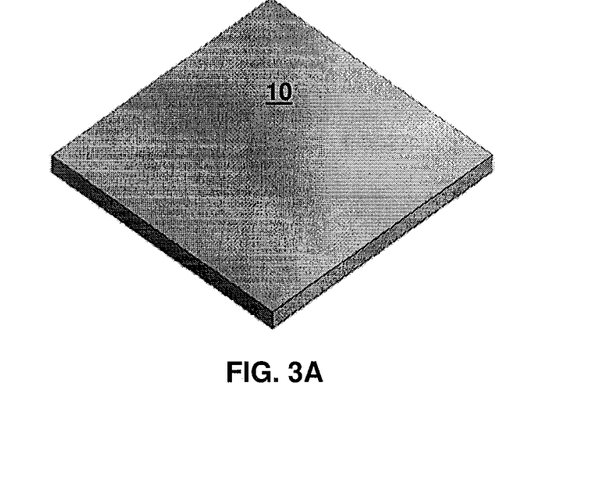
FIG. 3A illustrates a potential square view of the article as shown in FIG. 1.
Figure 3B:
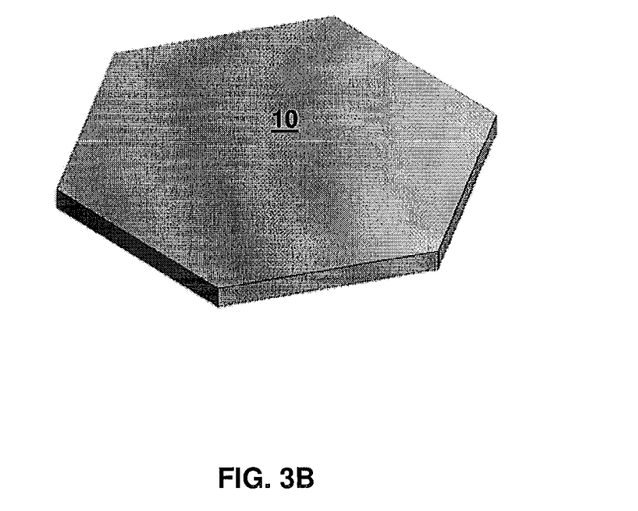
FIG. 3B illustrates a potential hexagonal view of the article as shown in FIG. 1.

Another embodiment of the presently disclosed invention is the change in the geometry of the filter media. The typical embodiment of the filter configuration is circular, as is shown in FIG. 1, but other shapes can achieve the same effectiveness in conjunction with the proper filtration support equipment, i.e. filter holders and housing. As shown in FIG. 3A and FIG. 3B, polygonal shapes, such as rectangular or hexagonal shapes, would be effective to reduce a material waste component and still achieve the same functionality. Another configuration may be a circular shape, wherein multiple diameters could be used to increase the filtration surface. Diameters of 25 to 500 mm are considered, with diameters of between 25 mm and 100 mm preferred. Further, thickness of the one piece solid phase extraction article 10 may be from 1 mm to 20 mm, with a thickness of from 2 mm to 3 mm preferred. Variations in the number of layers (sorbent and/or pre-filtration) included in a specific embodiment may influence the overall thickness of the article 10.

Certain embodiments of the presently disclosed invention provide for a solid phase extraction article which is a sheet that can be can be pleated so as to allow for inclusion in cartridge devices known in the art. To pleat the solid phase extraction sheet, it can be placed between two screens, scrims, or a screen and a scrim, and pleated by a variety of well-known methods using one of a variety of commercially available pleating machines. The screens and/or scrims help to cushion the sheet during pleating by reducing the amount of stress applied to the sheet by the pleating blades. The pleating can be traditional (in other words, parallel to the length of the cartridge device) or horizontal (in other words, perpendicular to the length of the cartridge device), as is described in U.S. Pat. No. 4,842,739.

Another embodiment of the presently disclosed invention is the change in the porosity of the porous matrix. Typically, filtration is assisted by a vacuum system providing intrusion or differential pressure to drive or pull the aqueous sample through the filter. By changing the porosity, the ability may exist to perform the filtration passively and without the aid of mechanical pressure. A change in porosity within multiple layers would also allow different substances to be filtered within a particular region. Porosities from 0.1 μm to 200 μm are considered, with porosities of 1 to 5 um preferred. In a specific embodiment of the presently disclosed invention, porosities of about 1 to 2 um are employed.

A preferred embodiment of the one piece solid phase extraction article 10 of the presently disclosed invention is a circular disk comprising a sorbent layer and a pre-filtration layer. The sorbent layer includes hydrophilic C-18 particles embedded in a glass fiber porous matrix. The pre-filtration layer includes a glass fiber porous matrix devoid of the hydrophilic C-18 particles. The one piece solid phase extraction article 10 may have a diameter of 47 mm, 90 mm, or 100 mm; and a thickness of from 2 to 3 mm. The porosity of the porous matrix in the sorbent layer and pre-filtration layer may be from 1-2 um, with a preferred porosity of 1.2 um.

Figure 4:
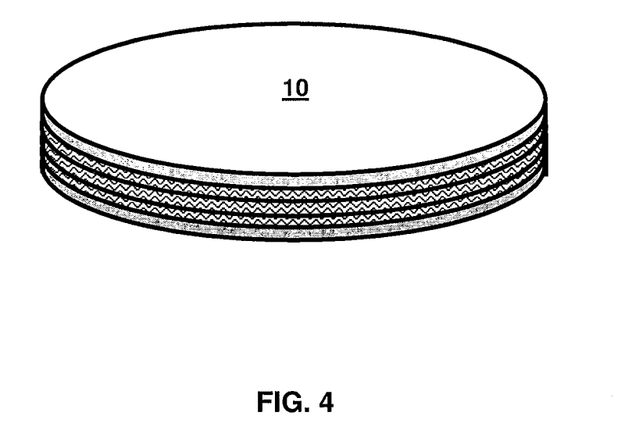
FIG. 4 illustrates a top perspective view of a multilayer solid phase extraction article in accordance with certain aspects of the presently disclosed invention.
Figure 5:
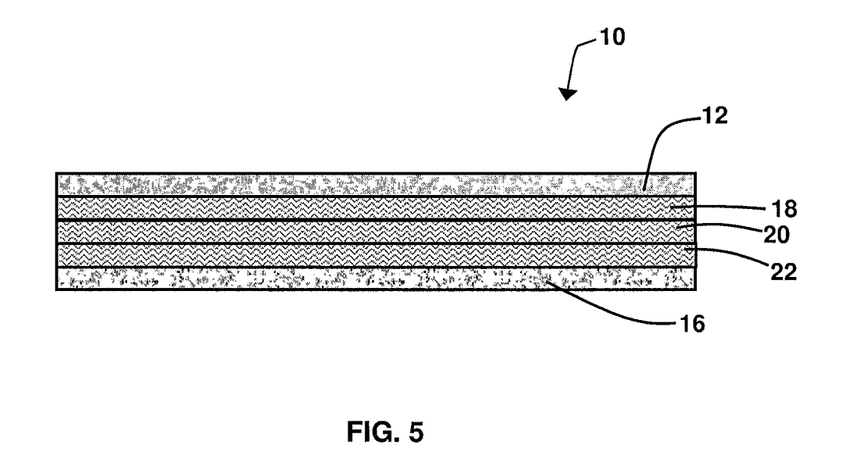
FIG. 5 illustrates a side view of the multilayered article configuration as shown in FIG. 4.

Further embodiments of the presently disclosed invention may also be achieved by a multi-layer one piece solid phase extraction article. A top perspective view of an exemplary one piece multi-layer solid phase extraction article is shown in FIG. 4, generally designated by the reference numeral 10. Such an article may have more than one sorbent layer, wherein each layer comprises water wettable sorptive particles embedded within a porous matrix. The one piece multi-layer solid phase extraction article may also comprise one or more pre-filtration layers (12, 16), as shown in FIG. 5. An exemplary multi-layer one piece solid phase extraction article may have more than one sorbent layer, such as the three sorbent layers (18, 20, 22) shown in FIG. 5. These sorbent layers may be as described previously, wherein each sorbent layer comprises any water wettable sorbent material embedded within any porous matrix; e.g., any sorbent material which may become activated or wet by water and does not require pre-conditioning with a polar solvent such as methanol. The sorbent may be any derivative of a monomeric phase type sorbent or a polymeric type sorbent material that is water wettable.

Figure 6:
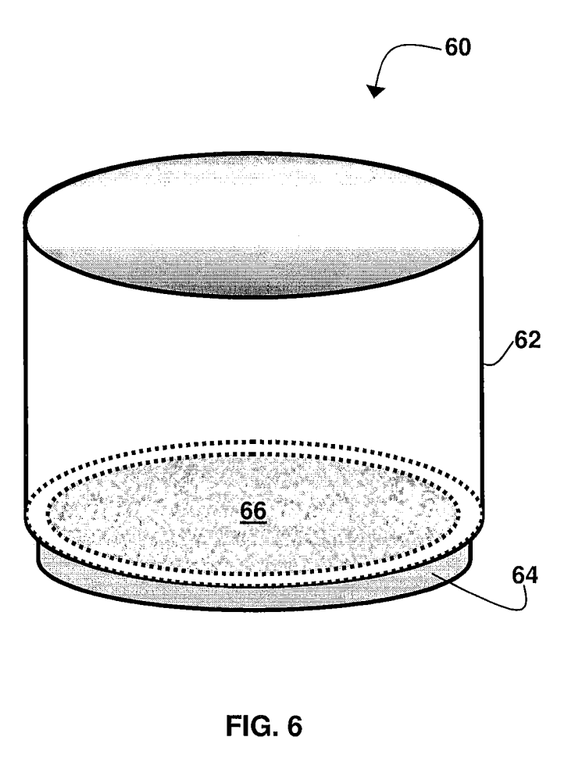
FIG. 6 illustrates a top perspective view of a filtration funnel comprising a solid phase extraction article in accordance with certain aspects of the presently disclosed invention.

Such an embodiment may allow multiple substances to be filtered for various tests. It may serve as an all-purpose filter useful in multiple tests and would not necessarily be specific to a single method or analytical test. Sorbents useful in such an embodiment may include cellulose fibers, polyacrylamides, activated carbon, functionalized C-8 sorbent material, functionalized C-18 sorbent material, and functionalized polystyrenedivinylbenzene. Further, the porous matrix of the sorbent layers and the optional pre-filtration layers may be plastic, synthetic fiber, paper media, sintered metal, glass fibers, or a synthetic membrane filter Further embodiments of the presently disclosed invention provide a filtration funnel comprising a one piece solid phase extraction article, such as any of the articles previously described. A top perspective view of an exemplary embodiment of such a filtration funnel is shown in FIG. 6, generally designated by reference numeral 60.

The filtration funnel may be attached to a filtration system comprising a vacuum source capable of pulling sample fluids placed in the funnel through the one piece solid phase extraction article. One such exemplary system is the StepSaver™ (Environmental Express; Charleston, S.C.), which is disclosed in U.S. Pat. No. 5,529,694, incorporated herein in its entirety by reference.

In embodiments, the filtration funnel may comprise an upper reservoir 62 for holding unfiltered fluid therein. The upper reservoir 62 may be able to contain liquid volumes of from 50 ml to 1500 ml. For example, an exemplary upper reservoir 62 may be able to contain 500 ml of a fluid sample. The filtration funnel also comprises an outlet 64 which may provide for attachment to a standard filtration system, such as the filtration system disclosed in U.S. Pat. No. 5,529,694. While the outlet 64 is shown to have a smaller diameter than the upper reservoir 62, any configuration which provides for attachment to a filtration system is envisioned and is within the scope of the presently disclosed invention. Further, while the upper reservoir 62 and outlet 64 are shown to have cylindrical profiles, other configurations are envisioned and are within the scope of the presently disclosed invention.

The one piece solid phase extraction article 66 may be disposed between the upper reservoir 62 and the outlet 64. The one piece solid phase extraction article 66 may comprise at least one sorbent layer as described above, and optionally may have one or more pre-filtration layers in contact with the top and/or bottom of the sorbent layer.

One embodiment of the filtration funnel comprising a one piece solid phase extraction article 60 may be disposable. Materials contemplated for construction of the filtration funnel body (upper reservoir 62 and outlet 64) includes at least plastics.

Various embodiments of the filtration funnel 60 may provide for a funnel which is a single piece construction, wherein the one piece solid phase extraction article 66 is integral and disposed within a region between the upper reservoir 62 and the outlet 64. In other embodiments, the one piece solid phase extraction article 66 may be disposed within an upper region of the outlet 64, which may be separable from the upper reservoir 62. In such an embodiment, the upper reservoir 62 may be separated from the outlet 64 comprising the one piece solid phase extraction article 66 during shipping or for storage before or after use.

Figure 7:
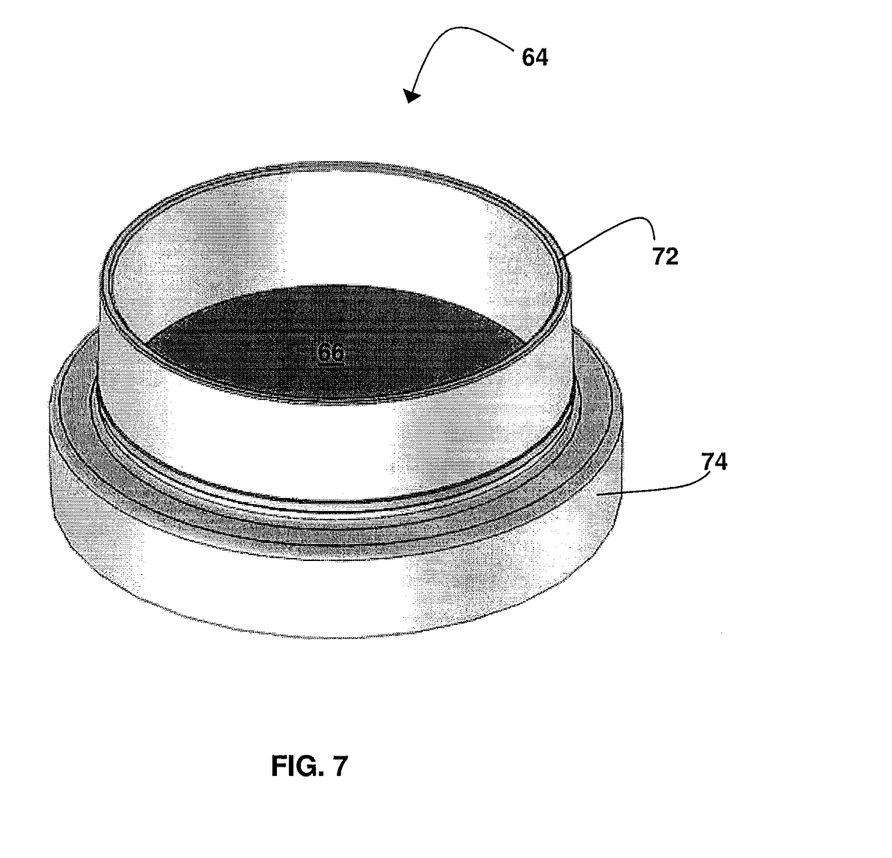
FIG. 7 illustrates a top perspective view of an outlet portion of the filtration funnel comprising a solid phase extraction article as shown in FIG. 6.

An exemplary embodiment of the filtration funnel of the presently disclosed invention is shown in FIG. 7, wherein the outlet 64 may be a discrete piece which is separable from the upper reservoir (62 as shown in FIG. 6). The one piece solid phase extraction article 66 may be disposed within the outlet 64 between an upper portion 72 designed to accept the upper reservoir (62 as shown in FIG. 6), and a lower portion 74 designed to connect to a collection container, such as the opening on a bottle (not shown).

Figure 8:
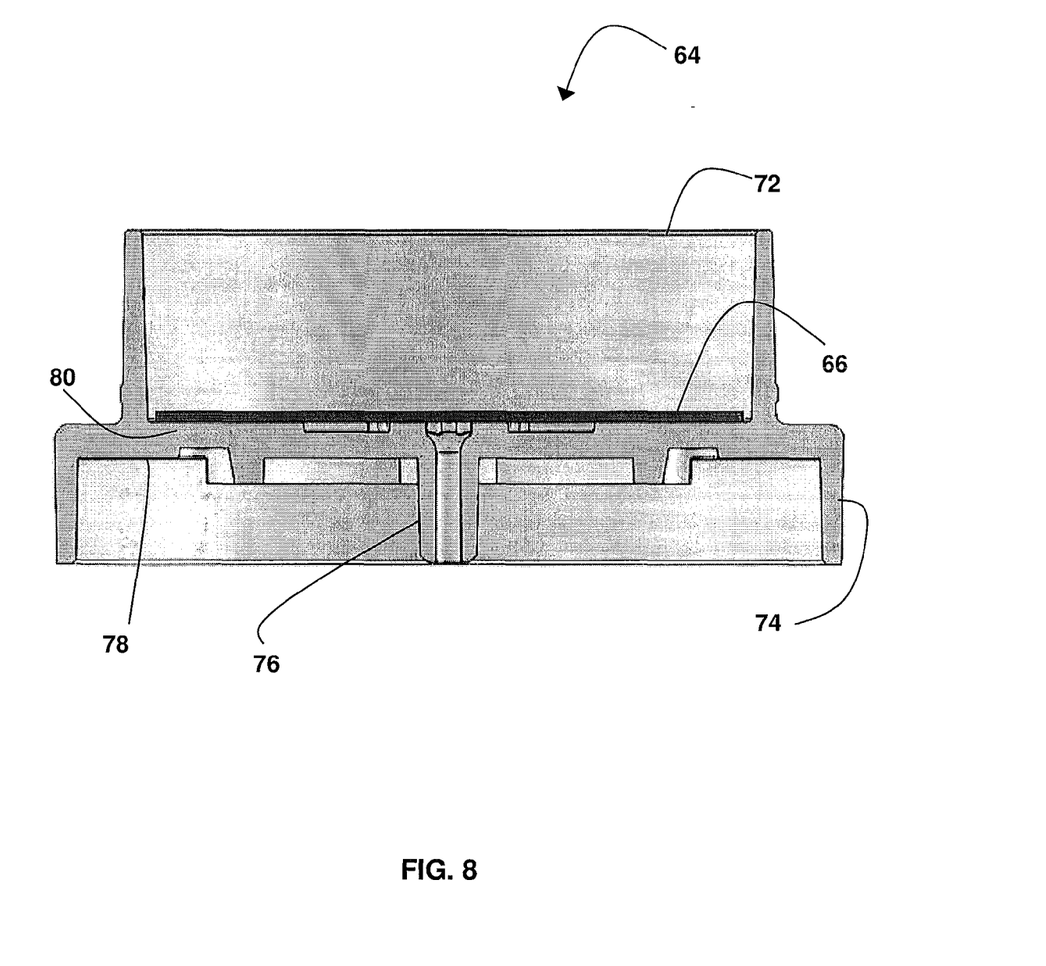
FIG. 8 illustrates a cross-sectional view of the outlet portion of the filtration funnel comprising a solid phase extraction article as shown in FIG. 6.

FIG. 8 shows a cross-sectional view of the outlet 64. As shown, the outlet 64 may have an upper portion 72 which is designed to accept the upper reservoir (62 as shown in FIG. 6). In the embodiment shown in FIG. 8, an opening at a bottom portion of the upper reservoir may fit snuggly around an outer circumference of the upper portion 72 of the outlet 64. In alternative embodiments, the opening at a bottom portion of the upper reservoir may fit snuggly around an inner circumference of the upper portion 72 of the outlet 64. In either configuration, the connection between the upper reservoir (62 as shown in FIG. 6) and the outlet 64 is water-tight so that no sample may leak from the filtration funnel 60 when assembled.

Further, the one piece solid phase extraction article 66 may be in contact with and/or supported by a support member 80. The support member 80 may have channels that collect a sample which has passed through the one piece solid phase extraction article 66 and route the now filtered sample to the outlet port 76. Further, the outlet 64 may also comprise a gasket 78 or other means that may provide an air-tight seal with an opening on a collection container, such as the opening on a bottle A further embodiment of the presently disclosed invention provides a method of concentrating by sorption at least one hexane extractable material from an organic fluid comprising: passing an organic fluid through a solid phase extraction article comprising at least one sorbent layer having water wettable monolithic polymeric sorptive particles embedded in a porous glass fiber matrix, wherein no pre-conditioning with a polar solvent is required prior to adsorption of an analyte by the sorptive particles. The method may further comprise eluting any adsorbed hexane extractable material by soaking the solid phase extraction article in n-hexane.

EXAMPLES

A study was performed to determine the HEM in various samples in accordance with EPA Method 1664 to compare a current filter configuration against embodiments of the presently disclosed invention for a validation on its performance. The study used real world samples as well as method blanks, which are samples of reagent water that are treated exactly as a real world sample in exposure to all glassware, equipment, solvents, and reagents. The results showed acceptable recovery of the HEM without the use of filter pre-conditioning steps, as is the typical standard procedure.

Example 1

Performance Testing

Currently, EPA Method 1664 is executed using a filter composed of a non-wettable C-18 material embedded in a porous glass fiber matrix. The filter is pre-conditioned using a polar solvent, such as methanol. Approximately 10 to 15 mL of methanol is used for this pre-conditioning step in a StepSaver™ vacuum system (Environmental Express; Charleston, S.C.). The polar solvent is then removed from the filter and replaced with de-ionized water to keep the C-18 sorbent material wet. Approximately 25-30 mL of de-ionized water is needed when using the StepSaver™ system.

To prove the presently disclosed invention meets all EPA Method 1664 requirements, a study was carried out to compare performance of an embodiment of the presently disclosed invention, Embodiment A, against a comparative filter known to provide acceptable results for the method: The UltraFlow™ filter disk (Environmental Express; Charleston, S.C.). The UltraFlow™ filter disk has been used for several years and provides quality results in SPE analysis for EPA Method 1664. Embodiment A comprises a sorbent layer which is a hydrophilic C-18 material embedded in a glass fiber and a pre-filtration layer which is a glass fiber. Both disks were run in a StepSaver™ extraction apparatus under similar laboratory conditions, except that the comparative UltraFlow™ filter disk was pre-conditioned as described above.

Both Embodiment A and the comparative UltraFlow™ filter disk were used to extract method detection limit standards, method blanks, and laboratory control standards. Further, both were used to extract ten "real world" samples along with two matrix spikes and two matrix spike duplicates to show comparable results. A matrix spike is an aliquot of an environmental sample to which known quantities of the analyte HEM have been added in the laboratory. These samples are prepared and analyzed exactly as a real world sample, and they are used to quantify any bias or imprecision caused by the sample solution. Background concentrations of HEM in the environmental samples are determined in a separate aliquot and the value is used to correct the matrix spike and matrix spike duplicate results.

Table 1 shows results for the method detection limit study performed using an Embodiment A and the comparative UltraFlow™ filter disk. The calculated method detection limit is below the EPA Method 1664 requirement of 1.4 mg/L and therefore acceptable.

TABLE 1

| Trial number | Embodiment A | UltraFlow ™ comparison |
|---|---|---|
| 1 | 4.6 mg/L | 5.0 mg/L |
| 2 | 4.6 mg/L | 4.8 mg/L |
| 3 | 4.4 mg/L | 5.2 mg/L |
| 4 | 4.7 mg/L | 4.8 mg/L |
| 5 | 4.9 mg/L | 4.8 mg/L |
| 6 | 4.7 mg/L | 4.9 mg/L |
| 7 | 4.5 mg/L | 4.9 mg/L |
| Calculated method detection limit | 0.5 mg/L | 0.46 mg/L |

Method detection limit standard of 5.0 mg/L analyzed

A series of five method blanks and five laboratory control standards were extracted using Embodiment A. Table 2 shows all blank results to be less than the reporting limit of 5.0 mg/L and all laboratory control standard recoveries to be well within the required limits of 78-114% for ongoing precision and recovery (as detailed in EPA Method 1664).

TABLE 2

| Trial number | Method Blank | Laboratory Control Standard |
|---|---|---|
| 1 | 1.3 mg/L | 35.8 mg/L (89.5% rec) |
| 2 | 1.1 mg/L | 37.9 mg/L (94.8% rec) |
| 3 | 1.6 mg/L | 35.0 mg/L (87.5% rec) |
| 4 | 2.3 mg/L | 35.8 mg/L (89.5% rec) |
| 5 | 0.5 mg/L | 39.2 mg/L (98.0% rec) |
| | reporting limit = 5.0 mg/L | laboratory control standard true value = 40.0 mg/L average % recovery = 91.9% |

The ten "real world" samples were collected and analyzed using Embodiment A and UltraFlow™ filter disks to show the extraction equivalency between the two. EPA Method 1664 states a precision requirement in Section 9.2.2.2 of 11%. As shown in Table 3, all Relative Percent Differences ("RPDs") between the results from the two filter disks were less than the 11% requirement.

TABLE 3

| Sample number | UltraFlow ™ comparison | Embodiment A | % RPD |
|---|---|---|---|
| 1 | 8.50 mg/L | 8.80 mg/L | 3.5% |
| 2 | 17.2 mg/L | 16.2 mg/L | 6.0% |
| 3 | 60.0 mg/L | 58.8 mg/L | 2.0% |
| 4 | 22.4 mg/L | 23.8 mg/L | 6.1% |
| 5 | 9.30 mg/L | 9.60 mg/L | 3.2% |
| 6 | 29.1 mg/L | 30.9 mg/L | 6.0% |
| 7 | 22.3 mg/L | 21.8 mg/L | 2.3% |
| 8 | 19.4 mg/L | 17.7 mg/L | 9.2% |
| 9 | 104 mg/L | 107 mg/L | 2.8% |
| 10 | 26.5 mg/L | 23.9 mg/L | 10.3% |

A set of matrix spike (MS) and matrix spike duplicate (MSD) samples were analyzed using samples collected from two different locations. Table 4 shows matrix spike and matrix spike duplicate results and recoveries for both Embodiment A and the UltraFlow™ filter disk comparison (spiked with 40 mg/L HEM). The first set of samples exhibited matrix interference effects on both Embodiment A and the UltraFlow™ filter disks. The second set of samples show acceptable recoveries (within the Method 1664 required 78-114% limits) for both Embodiment A and the UltraFlow™ filter disks.

TABLE 4

| Sample ID | UltraFlow ™ comparison | % Recovery | Embodiment A | % Recovery |
|---|---|---|---|---|
| MS#1 | 72.7 mg/L | 43% | 82.0 mg/L | 52% |
| MSD#1 | 73.5 mg/L | 45% | 81.2 mg/L | 50% |
| MS#2 | 48.5 mg/L | 97% | 44.9 mg/L | 91% |
| MSD#2 | 49.6 mg/L | 100% | 48.8 mg/L | 100% |

These studies show that embodiments of the presently disclosed invention provide equivalent extraction of HEM from water samples using EPA Method 1664A. Results from the method detection limit study, method blanks, and laboratory control standards show recoveries well within the required method limits. Real world sample results obtained using both an embodiment of the presently disclosed invention and the comparative UltraFlow™ filter disk exhibit excellent equivalency. The ability to use an extraction disk that does not require activation with a polar solvent such as methanol is a distinct advantage to the laboratory. It saves on procedure time, reagent costs and waste, and reduces the possibility of a method violation due to co-solvent introduction.

Example 2

Stability Testing

A second study was performed by filtering ten laboratory control standards (40 mg/L concentration), ten method detection limit standards (5.0 mg/L concentration), and ten method blanks through an embodiment of the presently disclosed invention. The filter assemblies and associated bottles were then stored in a refrigerator at 4° C. (+/−2° C.) for up to 30 days. Two laboratory control standards, method detection limit standards, and method blank filter disks were extracted every few days to determine stability of the HEM material on the filter disk and cleanliness of the blanks. Results are shown in Table 5.

TABLE 5

| Time held before extraction | Method blank | Method detection limit standard (5.0 mg/L) | % Recovery | Laboratory control standard (40.0 mg/L) | % Recovery |
|---|---|---|---|---|---|
| 5 days | 0.7 mg/L | 5.3 mg/L | 106% | 38.3 mg/L | 96% |
| 5 days | 0.5 mg/L | 4.7 mg/L | 94% | 37.8 mg/L | 95% |
| 9 days | 3.9 mg/L | 5.5 mg/L | 110% | 41.5 mg/L | 104% |
| 9 days | 3.4 mg/L | 5.4 mg/L | 108% | 39.7 mg/L | 99% |
| 13 days | −0.3 mg/L | 5.2 mg/L | 104% | 38.7 mg/L | 97% |
| 13 days | 0.3 mg/L | 5.3 mg/L | 106% | 38.7 mg/L | 97% |
| 21 days | 0.7 mg/L | 4.1 mg/L | 82% | 32.7 mg/L | 82% |
| 21 days | 0.4 mg/L | 5.1 mg/L | 102% | 34.2 mg/L | 86% |
| 30 days | 1.2 mg/L | 6.1 mg/L | 122% | 32.9 mg/L | 82% |
| 30 days | 2.2 mg/L | 6.1 mg/L | 122% | 34.1 mg/L | 85% |

The data shows good overall stability of the laboratory control standards over the 30 day test period. All results fall within the method defined acceptance range of 78-114%. While the method blank results are all below the laboratory's reporting limit of 5.0 mg/L, there were some instances of higher blank results on both the 9$^{th}$ and 30$^{th}$ days. The method detection limit standard recoveries also showed good stability during the study with the exception of the results from the 30$^{th}$ day. Embodiments of the presently disclosed invention demonstrated recoveries that were much higher than expected and may be due to the filters absorbing something over that time frame. This study does, however, show there are opportunities for filtration of samples in the field while maintaining the quality results required by the method.

The previous description is provided to enable any person skilled in the art to practice the various exemplary implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

While specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A one-piece solid phase extraction article comprising at least one sorbent layer having water wettable monolithic polymeric sorptive particles embedded in a porous matrix.

2. The one-piece solid phase extraction article according to Claim 1, wherein the water wettable monolithic polymeric sorptive particles are a hydrophilic polymeric gel.

3. The one-piece solid phase extraction article according to Claim 1, wherein the water wettable monolithic polymeric sorptive particles of the at least one sorbent layer are hydrophilic and are each separately selected from cellulose fibers, polyacrylamides, activated carbon, functionalized C-8 sorbent material, functionalized C-18 sorbent material, or functionalized polystyrenedivinylbenzene.

4. The one-piece solid phase extraction article according to Claim 1, wherein the water wettable monolithic polymeric sorptive particles of the at least one sorbent layer are a copolymer of stearyl methacrylate (SMA), poly(ethylene glycol) methyl ether methacrylate (PEGMEMA) and ethylene dimethacrylate (EDMA); or a copolymer of stearyl methacrylate (SMA), poly(ethylene glycol) methyl ether methacrylate (PEGMEA) and 1-propanol/1,4- butanediol.

5. The one-piece solid phase extraction article according to Claim 1, wherein the porous matrix is a plastic, a synthetic fiber, a paper media, a sintered metal, a glass fiber, a synthetic membrane filter, or a mixture thereof.

6. The one-piece solid phase extraction article according to Claim 5, wherein the porous matrix is a glass fiber.

7. The one-piece solid phase extraction article according to Claim 1, which is in the form of a circular disk or a polygon.

8. The one-piece solid phase extraction article according to Claim 1, further comprising:
   a pre-filtration layer,
   wherein the at least one sorbent layer is in contact with the pre-filtration layer.

9. The one-piece solid phase extraction article according to Claim 8, wherein the pre-filtration layer is selected from a plastic, a synthetic fiber, a paper media, a sintered metal, a glass fiber, a synthetic membrane filter, or a mixture thereof.

10. The one-piece solid phase extraction article according to Claim 1, further comprising:
   a first pre-filtration layer; and
   a second pre-filtration layer,
   wherein the at least one sorbent layer is disposed between and in contact with the first and second pre-filtration layers.

11. The one-piece solid phase extraction article according to Claim 10, wherein the first pre-filtration layer and second pre-filtration layer are each separately selected from a plastic, a synthetic fiber, a paper media, a sintered metal, a glass fiber, a synthetic membrane filter, or a mixture thereof.

12. The one-piece solid phase extraction article according to Claim 1, wherein the porosity of the porous matrix of the at least one sorbent layer is from 0.1 um to 200 um.

13. The one-piece solid phase extraction article according to Claim 8, wherein the porosity of the pre-filtration layer and the porous matrix of the at least one sorbent layer are each separately from 0.1 um to 200 um.

14. A filtration funnel for use on a vacuum filtration device, comprising:
    a reservoir for holding a fluid sample therein;
    an outlet for attachment to the vacuum filtration device; and
    a one piece solid phase extraction article comprising at least one sorbent layer having water wettable monolithic polymeric sorptive particles embedded in a porous matrix, the one piece solid phase extraction article disposed between the reservoir and the outlet so that
    wherein the fluid sample passes from the reservoir through the one piece solid phase extraction article and exits through the outlet.

15. The filtration funnel for use on a vacuum filtration device according to claim 14, wherein the water wettable monolithic polymeric sorptive particles of the at least one sorbent layer are hydrophilic and are each separately selected from cellulose fibers, polyacrylamides, activated carbon, functionalized C-8 sorbent material, functionalized C-18 sorbent material, or functionalized polystyrenedivinylbenzene.

16. The filtration funnel for use on a vacuum filtration device according to claim 14, wherein the porous matrix is a plastic, a synthetic fiber, a paper media, a sintered metal, a glass fiber, a synthetic membrane filter, or a mixture thereof.

17. The filtration funnel for use on a vacuum filtration device according to claim 14, wherein the one piece solid phase extraction article further comprises a pre-filtration layer, wherein the at least one sorbent layer is in contact with the pre-filtration layer.

18. The filtration funnel for use on a vacuum filtration device according to claim 17, wherein the pre-filtration layer is selected from a plastic, a synthetic fiber, a paper media, a sintered metal, a glass fiber, a synthetic membrane filter, or a mixture thereof.

19. A method of concentrating by sorption at least one hexane extractable material from an organic fluid comprising:
    passing an organic fluid through a one-piece solid phase extraction article comprising at least one sorbent layer having water wettable monolithic polymeric sorptive particles embedded in a porous glass fiber matrix,
    wherein no pre-conditioning with a polar solvent is required prior to adsorption of an analyte by the sorptive particles.

20. The method according to claim 19, further comprising:
    eluting any adsorbed hexane extractable material by soaking the solid phase extraction article in n-hexane.

* * * * *